US010617472B2

(12) United States Patent
Tennican et al.

(10) Patent No.: US 10,617,472 B2
(45) Date of Patent: Apr. 14, 2020

(54) ADHESIVE PATCH WITH ANTIMICROBIAL COMPOSITION (71) Applicant: Hyprotek, Inc., Spokane, WA (US)

(72) Inventors: Patrick O. Tennican, Spokane, WA (US); L. Myles Phipps, Shelton, WA (US)

(73) Assignee: Hyprotek, Inc., Spokane, WA (US)

( * ) Notice: Subject to any disclaimer, the term of this patent is extended or adjusted under 35 U.S.C. 154(b) by 0 days.

(21) Appl. No.: 13/757,423

(22) Filed: Feb. 1, 2013

(65) Prior Publication Data

US 2013/0204212 A1 Aug. 8, 2013

Related U.S. Application Data (60) Provisional application No. 61/595,635, filed on Feb. 6, 2012.

(51) Int. Cl.
*A61L 15/28* (2006.01)
*A61B 19/02* (2006.01)
*B65B 5/00* (2006.01)
*B05C 1/00* (2006.01)
*A61F 13/40* (2006.01)
*B65D 75/40* (2006.01)
(Continued)

(52) U.S. Cl.
CPC ...... *A61B 19/0256* (2013.01); *A61F 13/0253* (2013.01); *A61F 15/004* (2013.01); *A61M 5/158* (2013.01); *A61M 35/006* (2013.01); *B05C 1/00* (2013.01); *B65B 5/00* (2013.01); *B65D 75/40* (2013.01); *A61F 13/00063* (2013.01); *A61F 15/005* (2013.01); *A61M 2005/1586* (2013.01)

(58) Field of Classification Search
USPC ........ 424/445, 400, 616; 514/566, 574, 724; 604/304; 602/48, 54, 56–58, 61
See application file for complete search history.

(56) References Cited

U.S. PATENT DOCUMENTS 3,607,760 A 9/1971 McIntyre
3,851,649 A 12/1974 Villari
(Continued)

FOREIGN PATENT DOCUMENTS

CA 2656491 11/2014
CN 2511272 9/2002
(Continued)

OTHER PUBLICATIONS

PCT Search Report mailed May 15, 2013 for PCT application No. PCT/US13/24635, 10 pages.
(Continued)

*Primary Examiner* — Ophelia A Hawthorne
(74) *Attorney, Agent, or Firm* — Lee & Hayes, P.C.

(57) ABSTRACT

This disclosure describes example adhesive medical patches that may be used in combination with one or more antimicrobial agents to create and/or maintain an area of human skin that is free from contaminants. According to some embodiments, the disclosure describes that the adhesive patches may contain an adhesive material affixed to the perimeter of an impermeable backing According to some embodiments, the adhesive patch may also have a permeable layer containing an antimicrobial agent located interior to the adhesive material on the impermeable backing.

19 Claims, 3 Drawing Sheets (51) Int. Cl.
    *A61F 13/02*     (2006.01)
    *A61F 15/00*     (2006.01)
    *A61M 5/158*     (2006.01)
    *A61F 13/00*     (2006.01)

(56) References Cited

U.S. PATENT DOCUMENTS

| | | | |
|---|---|---|---|
| 3,860,348 A | | 1/1975 | Doyle |
| 4,188,234 A | * | 2/1980 | Budnick ............... C07F 9/3843 |
| | | | 106/267 |
| 4,291,697 A | | 9/1981 | Georgevich |
| 4,440,207 A | | 4/1984 | Genatempo et al. |
| 4,446,967 A | | 5/1984 | Halkyard |
| 4,564,010 A | | 1/1986 | Coughlan et al. |
| 4,588,400 A | | 5/1986 | Ring et al. |
| 4,696,393 A | | 9/1987 | Laipply |
| 4,811,847 A | | 3/1989 | Reif et al. |
| 4,813,210 A | | 3/1989 | Masuda et al. |
| 4,830,856 A | * | 5/1989 | Peppers ........................ 424/449 |
| 4,893,956 A | | 1/1990 | Wojcik et al. |
| 4,954,239 A | | 9/1990 | Mueller |
| 5,015,228 A | | 5/1991 | Columbus et al. |
| 5,041,264 A | | 8/1991 | Williams |
| 5,046,608 A | * | 9/1991 | Laipply ........................ 206/209 |
| 5,171,523 A | | 12/1992 | Williams |
| 5,438,984 A | | 8/1995 | Schoendorfer |
| 5,454,798 A | | 10/1995 | Kubalak et al. |
| 5,554,135 A | | 9/1996 | Menyhay |
| 5,556,375 A | | 9/1996 | Ewall |
| 5,569,207 A | * | 10/1996 | Gisselberg ............ A61M 25/02 |
| | | | 128/DIG. 26 |
| 5,637,080 A | | 6/1997 | Geng |
| 5,713,842 A | | 2/1998 | Kay |
| 5,716,636 A | | 2/1998 | Horstmann et al. |
| 5,730,530 A | | 3/1998 | Stoddard et al. |
| 5,732,716 A | | 3/1998 | Utecht |
| 5,772,031 A | | 6/1998 | Landis |
| 5,779,053 A | | 7/1998 | Partika et al. |
| 5,973,221 A | | 10/1999 | Collyer et al. |
| 6,063,029 A | * | 5/2000 | Saita et al. .................... 600/309 |
| 6,071,541 A | | 6/2000 | Murad |
| 6,168,800 B1 | | 1/2001 | Dobos et al. |
| 6,274,232 B1 | | 8/2001 | Otten et al. |
| 6,455,066 B1 | | 9/2002 | Fischer et al. |
| 6,769,546 B2 | | 8/2004 | Busch |
| 7,118,545 B2 | * | 10/2006 | Boyde ................... A61F 15/008 |
| | | | 602/43 |
| 7,282,186 B2 | | 10/2007 | Lake, Jr. et al. |
| 7,478,962 B2 | | 1/2009 | De Laforcade |
| 7,482,021 B1 | | 1/2009 | Tison et al. |
| 7,762,044 B2 | | 7/2010 | Clarke et al. |
| 7,770,726 B2 | | 8/2010 | Murray et al. |
| 7,780,794 B2 | | 8/2010 | Rogers et al. |
| 7,799,010 B2 | | 9/2010 | Tennican |
| 8,065,773 B2 | | 11/2011 | Vaillancourt et al. |
| 8,273,303 B2 | | 9/2012 | Ferlic et al. |
| 8,336,152 B2 | | 12/2012 | Vaillancourt et al. |
| 8,486,004 B1 | * | 7/2013 | Propp ................... A61M 25/02 |
| | | | 604/178 |
| 8,496,625 B2 | * | 7/2013 | Brugger et al. ................ 604/177 |
| 8,777,504 B2 | | 7/2014 | Shaw et al. |
| 8,778,387 B2 | | 7/2014 | Tennican et al. |
| 8,846,008 B2 | | 9/2014 | Tennican et al. |
| 9,522,001 B2 | | 12/2016 | Bui et al. |
| 2002/0185406 A1 | | 12/2002 | Massengale et al. |
| 2003/0007939 A1 | | 1/2003 | Murad |
| 2003/0138479 A1 | | 7/2003 | Mizota et al. |
| 2004/0037789 A1 | | 2/2004 | Moneuze et al. |
| 2004/0050402 A1 | | 3/2004 | D'Auria |
| 2004/0110841 A1 | | 6/2004 | Kite et al. |
| 2004/0129581 A1 | | 7/2004 | Tompkins |
| 2005/0034731 A1 | | 2/2005 | Rousseau et al. |
| 2005/0084521 A1 | | 4/2005 | Hamada et al. |
| 2005/0107732 A1 | | 5/2005 | Boyde |
| 2005/0129897 A1 | | 6/2005 | Zhou et al. |
| 2005/0255172 A1 | | 11/2005 | Omidbakhsh |
| 2005/0265773 A1 | | 12/2005 | De Laforcade |
| 2006/0062834 A1 | * | 3/2006 | Dixon ..................... A61L 15/28 |
| | | | 424/445 |
| 2006/0129117 A1 | * | 6/2006 | Malowaniec ................ 604/368 |
| 2006/0142684 A1 | | 6/2006 | Shanbrom |
| 2006/0151347 A1 | | 7/2006 | Grossman |
| 2006/0193816 A1 | | 8/2006 | Elfersy et al. |
| 2007/0014685 A1 | | 1/2007 | Halt, Sr. |
| 2007/0034538 A1 | | 2/2007 | Landis |
| 2007/0080017 A1 | | 4/2007 | Stickley |
| 2007/0179373 A1 | | 8/2007 | Pronovost |
| 2007/0246378 A1 | | 10/2007 | Cheaure et al. |
| 2007/0255193 A1 | | 11/2007 | Patel et al. |
| 2007/0274869 A1 | | 11/2007 | Rannikko et al. |
| 2008/0019889 A1 | | 1/2008 | Rogers et al. |
| 2008/0057136 A1 | | 3/2008 | Polyakov et al. |
| 2008/0063695 A1 | | 3/2008 | Vitaris |
| 2008/0119801 A1 | | 5/2008 | Moore |
| 2008/0181950 A1 | | 7/2008 | Bates et al. |
| 2009/0010998 A1 | | 1/2009 | Marchitto et al. |
| 2009/0012496 A1 | | 1/2009 | Tennican |
| 2009/0028750 A1 | | 1/2009 | Ryan |
| 2009/0036541 A1 | | 2/2009 | Mardis |
| 2009/0324508 A1 | | 12/2009 | Bobbert |
| 2010/0003067 A1 | | 1/2010 | Shaw et al. |
| 2010/0030170 A1 | | 2/2010 | Keller et al. |
| 2010/0050351 A1 | | 3/2010 | Colantonio et al. |
| 2010/0076362 A1 | * | 3/2010 | Utterberg ............ A61F 13/0246 |
| | | | 602/43 |
| 2010/0078336 A1 | | 4/2010 | Reyhan et al. |
| 2010/0163435 A1 | | 7/2010 | Fischer et al. |
| 2010/0172794 A1 | | 7/2010 | Ferlic et al. |
| 2010/0240799 A1 | | 9/2010 | Hofmann et al. |
| 2010/0260865 A1 | | 10/2010 | Kritzler |
| 2011/0052664 A1 | * | 3/2011 | Tennican et al. .............. 424/445 |
| 2011/0184382 A1 | | 7/2011 | Cady |
| 2011/0265834 A1 | | 11/2011 | Tennican |
| 2011/0295207 A1 | * | 12/2011 | Brugger ................... A61M 5/158 |
| | | | 604/164.04 |
| 2012/0288571 A1 | | 11/2012 | Tennican et al. |
| 2013/0138085 A1 | | 5/2013 | Tennican |
| 2013/0287860 A1 | | 10/2013 | Tennican et al. |
| 2014/0243725 A1 | | 8/2014 | Tennican et al. |
| 2017/0209229 A1 | | 7/2017 | Tennican et al. |

FOREIGN PATENT DOCUMENTS

| | | |
|---|---|---|
| CN | 2546003 | 4/2003 |
| CN | 2705167 | 6/2005 |
| CN | 1711845 | 12/2005 |
| CN | 1813097 | 8/2006 |
| CN | 101505815 | 8/2009 |
| CN | 201481841 | 5/2010 |
| CN | 102133421 | 7/2011 |
| CN | 103957988 | 7/2014 |
| EP | 0262792 | 4/1988 |
| EP | 1687039 | 1/2009 |
| EP | 2811988 | 12/2014 |
| EP | 2812048 | 12/2014 |
| EP | 13747071 | 12/2014 |
| FR | 2587207 | 3/1987 |
| GB | 350384 | 6/1931 |
| JP | S34018480 | 11/1959 |
| JP | S59500801 | 5/1984 |
| JP | S61501019 | 5/1986 |
| JP | 02180278 | 7/1990 |
| JP | H02149225 | 12/1990 |
| JP | H05044111 | 6/1993 |
| JP | 07500751 | 1/1995 |
| JP | H07043749 | 9/1995 |
| JP | H08191855 | 7/1996 |
| JP | H08318975 | 12/1996 |
| JP | 10110268 | 4/1998 |
| JP | H10511999 | 11/1998 |
| JP | 2001510704 | 8/2001 |
| JP | 2001525688 | 12/2001 |
| JP | 2002529545 | 9/2002 |
| JP | 2003277256 | 10/2003 |

(56) References Cited

FOREIGN PATENT DOCUMENTS

| | | |
|---|---|---|
| JP | 2004049540 | 2/2004 |
| JP | 2004351632 | 12/2004 |
| JP | 2005511147 | 4/2005 |
| JP | 2005120008 | 5/2005 |
| JP | 2005350571 A | 12/2005 |
| JP | 2005353566 | 12/2005 |
| JP | 2006503647 | 2/2006 |
| JP | 2006516003 | 6/2006 |
| JP | 2006232340 | 9/2006 |
| JP | 2006526664 | 11/2006 |
| JP | 2007044258 | 2/2007 |
| JP | 2007505093 | 3/2007 |
| JP | 2007536261 | 12/2007 |
| JP | 2008503485 | 2/2008 |
| JP | 2009519312 | 5/2009 |
| JP | 2009537250 | 10/2009 |
| JP | 2011056183 | 3/2011 |
| JP | 2011074014 | 4/2011 |
| JP | 2013503713 | 2/2013 |
| MX | 2014006412 | 11/2011 |
| WO | WO8503275 | 8/1985 |
| WO | WO9204923 | 4/1992 |
| WO | WO9308777 | 5/1993 |
| WO | WO0156540 | 8/2001 |
| WO | WO2004091675 | 10/2004 |
| WO | WO2004108091 | 12/2004 |
| WO | WO2005003436 | 1/2005 |
| WO | WO2005025486 | 3/2005 |
| WO | WO2005062896 | 7/2005 |
| WO | WO2005089341 | 9/2005 |
| WO | WO2006009853 | 1/2006 |
| WO | WO2006/089139 A2 | 8/2006 |
| WO | WO2007068938 | 6/2007 |
| WO | WO2007137056 | 11/2007 |
| WO | WO2008003779 | 1/2008 |
| WO | WO2008009925 | 1/2008 |
| WO | WO2008063648 | 5/2008 |
| WO | WO2009076718 | 6/2009 |
| WO | WO2009136957 | 11/2009 |
| WO | WO2010128554 | 11/2010 |
| WO | WO2010131253 | 11/2010 |
| WO | WO2011028965 | 3/2011 |
| WO | WO2011019132 | 7/2011 |
| WO | WO2011091322 | 7/2011 |
| WO | WO2011163124 | 12/2011 |
| WO | WO2012007929 | 1/2012 |
| WO | WO2013082187 | 6/2013 |
| WO | WO2014025994 | 2/2014 |

OTHER PUBLICATIONS

PCT Search Report mailed May 13, 2013 for PCT application No. PCT/US13/24644, 10 pages.

PCT Search Report mailed May 15, 2013 for PCT application No. PCT/US13/24651, 12 pages.

PCT Search report mailed May 31, 2013 for PCT application No. PCT/US13/24649, 14 pages.

Translated Japanese Office Action mailed Dec. 24, 2014 for Japanese patent application No. 2012-550177, a counterpart foreign application of U.S. Pat. No. 8,846,008, 4 pages.

Mexican Office Action mailed Jan. 13, 2015 for Mexican patent application No. MX/a/2012/002746, a counterpart foreign application of U.S. Pat. No. 8,778,387, 2 pages.

Office Action for U.S. Appl. No. 14/271,365, mailed on Jan. 23, 2015, Patrick O. Tennican, "Antimicrobial Medical Dressings and Protecting Wounds and Catheter Sites", 8 pages.

Office Action for U.S. Appl. No. 13/757,465, mailed on Feb. 9, 2015, Patrick O. Tennican, "Combined Cap Applicators", 14 pages.

Office Action for U.S. Appl. No. 13/934,135, mailed on Mar. 12, 2015, Patrick O. Tennican, "Antimicrobial Agents and Methods of Use", 14 pages.

Translated Russian Office Action mailed Jan. 23, 2015 for Russian patent applcation No. 2012136147, a counterpart foreign application of US patent application No. , pages.

Australian Office Action mailed Nov. 4, 2013 for Australian patent application No. 2010289415, a counterpart foreign application of U.S. Appl. No. 12/874,188, 3 pages.

Australian Office Action mailed Mar. 13, 2014 for Australian patent application No. 2011207398, a counterpart foreign application of U.S. Appl. No. 13/554,962, 3 pages.

Translated Chinese Office Action mailed Oct. 17, 2013 for Chinese patent application No. 201180006632.3, a counterpart foreign application of U.S. Appl. No. 13/554,962, 13 page.

Translated Chinese Office Action mailed Oct. 23, 2014 for Chinese patent application No. 201080047665.8, a counterpart foreign application of U.S. Pat. No. 8,778,387, 13 pages.

Translated Chinese Office Action mailed Apr. 10, 2014 for Chinese patent application No. 201180006632.3, a counterpart foreign application of U.S. Appl. No. 13/554,962, 19 pages.

Translated Chinese Office Action mailed Apr. 22, 2014 for Chinese patent application No. 201080047665.8, a counterpart foreign application of U.S. Appl. No. 12/874,188, 17 pages.

Translated Chinese Office Action mailed Aug. 12, 2013 for Chinese patent application No. 201080047665.8, a counterpart foreign application of U.S. Appl. No. 12/874,188, 13 pages.

Translated Chinese Office Action mailed Sep. 25, 2014 for Chinese patent application No. 201180006632.3, a counterpart foreign application of U.S. Appl. No. 13/554,962, 19 pages.

European Office Action mailed Sep. 12, 2014 for European patent application No. 11701925.7, a counterpart foreign application of U.S. Pat. No. 8,846,008, 5 pages.

European Search Report mailed Apr. 23, 2014 for European patent application No. , 11 pages.

Final Office Action for U.S. Appl. No. 13/554,962, mailed on Dec. 5, 2013, Patrick O. Tennican, "Antimicrobial Agents and Methods of Use", 14 pages.

Hospenthal et al., "Guidelines for the Prevention of Infections After Combat-Related Injuries", Journal of Trauma Injury, Infection, and Critical Care, vol. 64, No. 3, Mar. 2008, pp. S211-S220.

Translated Japanese Office Action mailed Aug. 19, 2014 for Japanese patent application No. 2012-528071, a counterpart foreign application of U.S. Pat. No. 8,778,387, 10 pages.

Japanese Patent No. JP6501857, which corresponds to International Patent Publication No. WO92/04923.

McGee et al., "Preventing Complications of Central Venous Catheterization", The New England Journal of Medicine, vol. 348, No. 12, Mar. 20, 2003, pp. 1123-1133.

Mexican Office Action mailed Jul. 2, 2014 for Mexican patent application No. MX/a/2012/008482, a counterpart foreign application of U.S. Appl. No. 13/554,962, 2 pages.

Mexican Office Action mailed May 26, 2014 for Mexican patent application No. MX/a/2012/002746, a counterpart foreign application of U.S. Pat. No. 8,778,387, 4 pages.

Office Action for U.S. Appl. No. 13/924,410, mailed on Nov. 22, 2013, Patrick O. Tennican, "Antimicrobial Agents and Methods of Use", 15 pages.

Final Office Action for U.S. Appl. No 12/874,188, mailed Dec. 19, 2012, Patrick O. Tennican et al., "Antimicrobial Medical Dressings and Protecting Wounds and Catheter Sites", 6 pages.

Non-Final Office Action for US Patent Application mailed on Feb. 15, 2013, Patrick O. Tennican et al., "Antimicrobial Agents and Methods of Use", 12 pages.

Non-Final Office Action for U.S. Appl. No. 12/874,188, mailed Feb. 7, 2014, Patrick O. Tennican et al., "Antimicrobial Medical Dressings and Protecting Wounds and Catheter Sites", 6 pages.

Office Action for U.S. Appl. No. 13/924,410, mailed on Mar. 28, 2014, Patrick O. Tennican, "Antimicrobial Agents and Methods of Use", 18 pages.

Non-Final Office Action for U.S. Appl. No. 12/874,188, mailed Jun. 29, 2012, Patrick O. Tennican et al., "Antimicrobial Medical Dressings and Protecting Wounds and Catheter Sites", 6 pages.

Office action for U.S. Appl. No. 13/757,318, mailed on Aug. 26, 2014, Tennican, "Antiseptic Applicators and Packaging Techniques", 9 pages.

(56) References Cited

OTHER PUBLICATIONS

Office action for U.S. Appl. No. 12/874,188, mailed on Sep. 10, 2013, Tennican et al., "Antimicrobial Medical Dressings and Protecting Wounds and Catheter Sites", 6 pages.
Office action for U.S. Appl. No. 14/271,365, mailed on Sep. 11, 2014, Tennican et al., "Antimicrobial Medical Dressings and Protecting Wounds and Catheter Sites", 7 pages.
PCT Search Report mailed May 20, 2011 for PCT Appliction No. PCT/US10/47756.
PCT Search Report mailed Aug. 1, 2011 for PCT application No. PCT/US11/22150.
Singhal et al., "Wound Infection", eMedicine from WebMD <<http://www.emedicine.medscape.com>>, Updated Sep. 15, 2009, 32 pages.
"VERSENE Acid—Solubility", The Dow Chemical Company, Sep. 15, 2010, pp. 1-3.
"VERSENE NA Disodium EDTA Chelating Agent", The Dow Chemical Company, Oct. 2009, pp. 1-2.
Translated Chinese Office Action mailed Apr. 8, 2015 for Chinese patent application No. 201180006632.3, a counterpart foreign application of U.S. Pat. No. 8,846,008, 19 pages.
Translated Chinese Office Action mailed Apr. 9, 2015 for Chinese patent application No. 201080047665.8, a counterpart foreign application of U.S. Pat. No. 8,778,387, 8 pages.
Translated Japanese Office Action mailed Apr. 14, 2015 for Japanese patent application No. 2012-528071, a counterpart foreign application of U.S. Pat. No. 8,778,387, 9 pages.
Final Office Action for U.S. Appl. No. 13/757,465, mailed on May 28, 2015, Patrick O. Tennican, "Combined Cap Applicators", 15 pages.
Final Office Action for U.S. Appl. No. 14/271,365, mailed on Jun. 1, 2015, Patrick O. Tennican, "Antimicrobial Medical Dressings and Protecting Wounds and Catheter Sites", 10 pages.
Final Office Action for U.S. Appl. No. 13/934,135, mailed on Jul. 7, 2015, Patrick O. Tennican, "Antimicrobial Agents and Methods of Use", 9 pages.
Carson, "Local Anesthetics That Metabolize to 2,6-Xylidine or o-Toluidine," Integrated Laboratory Systems, Oct. 2000, 329 pages.
Extended European Search Report mailed Mo Sep. 10, 2015 for European Patent Application No. 13747071.2, 8 pages.
Extended European Search Report mailed Sep. 11, 2015 for European Patent Application 13746209.9, 6 pages.
Extended European Search Report mailed Sep. 17, 2015 for European patent application No. 13746984.7, 7 pages.
Extended European Search Report mailed Sep. 18, 2015 for European Patent Application No. 13746515.9, 7 pages.
Translated Japanese Office Action mailed Aug. 11, 2015 for Japanese patent application No. 2012-550177, a counterpart foreign application of U.S. Pat. No. 8,846,008, 4 pages.
Nouri-Nigjeh et al., "Lidocaine oxidation by electrogenerated reactive oxygen species in the light of oxidative drug metabolism," Electrochemistry in the Mimicry of Oxidative Drug Metabolism, 2010, pp. 43-64.
Office Action for U.S. Appl. No. 13/757,381, mailed on Jul. 1, 2015, Patrick O. Tennican, "Portable Medical Device Protectors", 9 pages.
Office Action for U.S. Appl. No. 14/271,365, mailed on Oct. 2, 2015, Patrick O. Tennican, "Antimicrobial Medical Dressings and Protecting Wounds and Catheter Sites", 9 pages.
Australian Office Action mailed Nov. 16, 2015 for Australian patent application No. 2013217602, a counterpart foreign application of U.S. Pat. No. 9,039,967, 3 pages.
Australian Office Action mailed Nov. 30, 2015 for Australian patent application No. 2013217603, a counterpart foreign application of U.S. Appl. No. 13/757,381, 3 pages.
Translated Chinese Office Action mailed Nov. 4, 2015 for Chinese patent application No. 201380008084.7, a counterpart foreign application of U.S. Pat. No. 9,192,443, 22 pages.
Translated Chinese Office Action mailed Nov. 27, 2015 for Chinese patent application No. 201380007894.0, a counterpart foreign application of U.S. Appl. No. 13/757,381, 18 pages.
Chinese Office Action dated Jan. 26, 2016 for Chinese Patent Application No. 201380006373.3, a counterpart foreign application of U.S. Appl. No. 13/757,423, 16 pages.
Chinese Office Action dated Dec. 1, 2015 for Chinese patent application No. 201380007893.6, a counterpart foreign application of U.S. Pat. No. 9,039,967, 19 pages.
CN101279102 corresponds to U.S. Patent Application Publication No. 2008/0063695 cited herewith.
European Office Action dated Jan. 19, 2016 for European patent application No. 13746209.9, a counterpart foreign application of U.S. Pat. No. 9,039,967, 4 pages.
Office action for U.S. Appl. No. 13/757,381, dated Nov. 25, 2015, Tennican et al., "Portable Medical Device Protectors", 7 pages.
Office action for U.S. Appl. No. 14/271,365, dated Feb. 22, 2016, Tennican et al., "Antimicrobial Medical Dressings and Protecting Wounds and Catheter Sites", 13 pages.
Office action for U.S. Appl. No. 13/757,381, dated Mar. 7, 2016, Tennican et al., "Portable Medical Device Protectors", 7 pages.
European Office Action dated Jun. 3, 2016 for European Patent Application No. 13746209.9, a counterpart foreign application of U.S. Pat. No. 9,039,967, 4 pages.
Chinese Office Action dated Jun. 1, 2016 for Chinese Patent Application No. 201380008084.7, a counterpart foreign application of U.S. Pat. No. 9,192,443.
Translated copy of the Chinese Office Action dated Jun. 21, 2016 for Chinese Patent Application No. 201380007894.0, a counterpart foreign application of U.S. Appl. No. 13/757,381, 10 pages.
Australian Office Action dated Jul. 21, 2016 for Australian Patent Application No. 2013217602, a counterpart foreign application of U.S. Pat. No. 9,039,967, 4 pages.
European Office Action dated Mar. 29, 2016 for European patent application No. 11701925.7, a counterpart foreign applcation of U.S. Pat. No. 8,846,008, 5 pages.
European Office Action dated Mar. 30, 2016 for European patent application No. 13747071.2, a counterpart foreign application of U.S. Appl. No. 13/757,381, 4 pages.
Office action for U.S. Appl. No. 14/271,365, dated May 5, 2016, Tennican et al., "Antimicrobial Medical Dressings and Protecting Wounds and Catheter Sites", 9 pages.
Chinese Office Action dated Aug. 2, 2016 for Chinese patent application No. CN201380007893.6, a counterpart foreign application of U.S. Pat. No. 9,039,967, 20 pages.
Australian Office Action dated Sep. 29, 2016, for Australian patent application No. 2013217607, a counterpart foreiign application of U.S. Pat. No. 9,192,443, 4 pages.
European Office Action dated Oct. 7, 2016 for European Patent Application No. 13747071.2, a coutnerpart foreign application of U.S. Pat. No. 13/757,381, 4 pages.
European Office Action dated Feb. 14, 2017 for European Patent Application No. 13747071.2, a counterpart foreign application of U.S. Appl. No. 13/757;381, 5 pages.
European Office Action dated Mar. 24, 2017 for European Patent Application No. 10814534.3, a counterpart foreign application of U.S. Pat. No. 8,778,387, 4 pages.
Australian Office Action dated Feb. 3, 2017 for Australian Patent Application No. 2013217607, a counterpart foreign application of U.S. Pat. No. 9,192,443, 4 pages.
Chinese Office Action dated Jan. 26, 2017 for Chinese Patent Application No. 201380007893.6, a counterpart foreign application of U.S. Pat. No. 9,039,967, 12 pages.
Japanese Office Action dated Jan. 31, 2017 for Japanese Patent Application No. 2014-555818, a counterpart foreign application of U.S. Appl. No. 13/757,381, 15 pages.
Japanese Office Action mailed Feb. 28, 2017 for Japanese Patent Application No. 2014-555821, a counterpart foreign application of U.S. Appl. No. 13/757,423, 5 pages.
Australian Office Action dated Nov. 24, 2016 for Australian patent application No. 2013217606, a counterpart foreign application of U.S. Appl. No. 13/757,423, 3 pages.
Canadian Office Action dated Nov. 8, 2016 for Canadian patent application No. 2772042, a counterpart foreign application of U.S. Pat. No. 8,778,337, 3 pages.

(56) References Cited

OTHER PUBLICATIONS

Chinese Office Action dated Oct. 13, 2016 for Chinese patent application No. 201380006373,3, a counerpart foreign application of U.S. Appl. No. 13/757,423, 17 pages.
Chinese Office Action dated Dec. 8, 2016 for Chinese Patent Application No. 201330008084.7, a counterpart foreign application of U.S. Pat. No. 9,192,443, 23 pages.
European Office Action dated Dec. 9, 2016 for European Patent Application No. 13746984.7, a counterpart foreiign application of U.S. Pat. No. 9,192,443, 4 pages.
Japanese Office Action dated Oct. 25, 2016 for Japanese Patent Application No. 2016-000215, a counterpart foreign application of U.S. Pat. No. 8,846,008, 11 pages.
Japanese Office Action dated Nov. 22, 2016 for Japanese Patent Application No. 2014-555816, a counterpart foreign application of U.S. Pat. No, 9,039,967, 14 pages.
Japanese Office Action dated Oct. 18, 2016 for Japanese Patent Application No. 2014-555822, a counterpart foreign application of U.S. Pat. No. 9,192,443, 13 pages.
Japanese Office Action dated Oct. 25, 2016 for Japanese Patent Application No. 2014-555821, a counterpart foreign application of U.S. Appl. No. 13/757,423, 9 pages.
Korean Office Action dated Dec. 1, 2016 for Korean Patent Application No. 10-2012-7019446, a counterpart foreign application of U.S. Pat. No. 8,846,008.
Mexican Office Action dated Oct. 24, 2016 for Mexican patent application No. MX/a/2014/009435, a counterpart foreign application of U.S. Pat. No. 9,039,967.
Office Action for U.S. Appl. No. 13/757,381, dated Dec. 12, 2016, Tennican et al., "Portable Medical Device Protectors", 7 pages.
"The Infection", vol. 23, No. 3, 1998, pp. 107-111 (Document in Japanese, translation not available).
Canadian Office Action dated Jan. 12, 2017 for Canadian patent application No. 2786880, a counterpart foreign application of U.S. Pat. No. 8,846,008, 4 pages.
Chinese Office Action dated Dec. 30, 2016 for Chinese patent application No. 201380007894.0, a counterpart foreign application of U.S. Appl. No. 13/757,381, 16 pages.
Office Action for U.S. Appl. No. 14/271,365, dated Feb. 3, 2017, Patrick O. Tennican, "Antimicrobial Medical Dressings and Protecting Wounds and Catheter Sites", 7 pages.
Chinese Office Action dated Jun. 14, 2017 for Chinese Patent Application No. 201380006373.3, a counterpart foreign application of U.S. Appl. No. 13/757,423, 12 pages.
European Office Action dated May 30, 2017 for European Patent Application No. 13746984.7, a counterpart foreign application of U.S. Pat. No. 9,192,443, 3 pages.
Japanese Office Action dated May 9, 2017 for Japanese Patent Application No. 2014-555816, a counterpart foreign application of U.S. Pat. No. 9,039,967, 7 pages.
European Office Action dated May 3, 2017 for European Patent Application No. 13747071.2, a counterpart foreign application of U.S. Appl. No. 13/757,381, 4 pages.
Japanese Office Action dated Mar. 28, 2017 for Japanese patent application No. 2014-555822, a counterpart foreign application of U.S. Pat. No. 9,192,443, 15 pages.
Mexican Office Action dated Mar. 15, 2017 for Mexican patent application No. MX/a/2014/0094 5, a counterpart foreign application of U.S. Pat. No. 9,039,967.
Brazilian Office Action dated Sep. 10, 2019 for Brazilian Patent Application No. BR1120140192332, a counterpart of U.S. Appl. No. 13/757,423, 7 pages.
Brazilian Office Action dated Feb. 4, 2019 for Brazilian patent application No. BR1120140186880, a counterpart foreign application of U.S. Pat. No. 9,039,967.
Brazilian Office Action dated Feb. 4, 2019 for Brazilian patent application No. BR1120140186677, a counterpart foreign application of U.S. Appl. No. 13/757,381.

Canadian Office Action dated Dec. 17, 2018 for Canadian Patent Application No. 2,863,702, a counterpart of U.S. Pat. No. 9,192,443, 3 pages.
Canadian Office Action dated Dec. 6, 2018 for Canadian Patent Application No. 2,863,855, a of U.S. Appl. No. 13/757,423, 4 pages.
Canadian Office Action dated Apr. 2, 2019 for Canadian Patent Application No. 2,863,841, a counterpart of U.S. Pat. No. 9,039,967, 4 pages.
Canadian Office Action dated Aug. 16, 2017 for Canadian Patent Application No. 2772042, a counterpart foreign application of U.S. Pat. No. 8,778,387, 5 pages.
Chinese Office Action dated Nov. 22, 2017 for Chinese Patent Application No. 201380007893.6, a counterpart foreign application of U.S. Pat. No. 9,039,967, 16 pages.
Chinese Office Action dated Jun. 8l, 2018 for Chinese patent application No. 201380007893.6, a counterpart foreign application of U.S. Pat. No. 9,039,967.
Chinese Office Action dated Jul. 2, 2018 for Chinese patent application No. 201380006373.3, a counterpart foreign application of U.S. Appl. No. 13/757,423, 14 pages.
Chinese Office Action dated Jul. 25, 2017 for Chinese patent application No. 201380007894.0, a counterpart foreign application of U.S. Appl. No. 13/757,381.
European Office Action dated Jan. 30, 2018 for European patent application No. 13747071.2, a counterpart foreign application of U.S. Appl. No. 13/757,381, 3 pages.
European Office Action dated Jul. 21, 2017 for European Patent Application No. 13746515.9, a counterpart foreign application of U.S. Appl. No. 13/757,423, 7 pages.
European Office Action dated Sep. 1, 2017 for European patent application No. EP13747071.2, a counterpart foreign application of U.S. Appl. No. 13/757,381, 4 pages.
Indian Office Action dated Jan. 17, 2019 for Indian Patent Application No. 1869/DELNP/2012, a counterpart of U.S. Pat. No. 8,778,387, 6 pages.
Indian Office Action dated Oct. 12, 2017 for Indian patent application No. 6488/DELNP/2012, a counterpart foreign application of U.S. Pat. No. 8,846,008, 6 pages.
Indian Office Action dated Mar. 13, 2019 for Indian Patent Application No. 6383/DELNP/2014, a counter part of U.S. Pat. No. 9,039,967, 7 pages.
Indian Office Action dated May 8, 2018 for Indian patent application No. , a counterpart foreign of US patent application No. 6503/DELNP/2014, 6 pages.
Indian Office Action dated Jun. 12, 2018 for Indian patent application No. 6464/DELNP/2014, a counterpart foreign application of U.S. Appl. No. 13/757,423, 7 pages.
Japanese Office Action dated Oct. 30, 2018 for Japanese patent application No. 2014-555822, a counterpart foreign application of U.S. Pat. No. 9,192,443, 6 pages.
Japanese Office Action dated Nov. 13, 2018 for Japanese Patent Application No. 2014-555816, a counterpart to U.S. Appl. No. 13/757,318, 13 pages.
Japanese Office Action dated Nov. 14, 2017 for Japanese patent application No. 2014-555816, a counterpart foreign application of U.S. Pat. No. 9,039,967.
Japanese Office Action dated Dec. 4, 2018 for Japanese Patent Application No. 2017-171461, a counterpart of U.S. Pat. No. 9,039,967, 12 pages.
Japanese Office Action dated Mar. 19, 2019 for Japanese Patent Application No. 2014-555816, a counterpart of U.S. Pat. No. 9,039,967, 6 pages.
Japanese Office Action dated May 8, 2018 for Japanese patent application No. 2017-009173, a counterpart foreign application of U.S. Appl. No. 13/757,423, 7 pages.
Japanese Office Action dated Jun. 20, 2017 for Japanese patent application No. 2014-555818, a counterpart foreign application of U.S. Appl. No. 13/757,381, 5 pages.
Japanese Office Action dated Jul. 10, 2018 for Japanese patent application No. , a counterpart foreign application of U.S. Pat. No. 9,039,967, 17 pages.

(56) References Cited

OTHER PUBLICATIONS

Japanese Office Action dated Aug. 25, 2017 for Japanese Patent Application No. 2014-555821, a counterpart foreign application of U.S. Appl. No. 13/757,423, 9 pages.

Japanes Office Action dated Sep. 4, 2017 for Japanese patent application No. 2014-555822, a counterpart foreign application of U.S. Pat. No. 9,192,443.

Mexican Office Action dated Jun. 5, 2018 for Mexican patent application No. MX/a/2014/009432, a counterpart foreign application of U.S. Pat. No. 9,192,443.

Mexican Office Action dated Jun. 5, 2018 for Mexican patent application No. MX/a/2014/009433, a counterpart foreign application of U.S. Appl. No. 13/757,423.

Mexican Office Action dated Jun. 5, 2018 for Mexican patent application No. MX/a/2014/009434, a counterpart foreign application of U.S. Appl. No. 13/757,381.

Office Action for U.S. Appl. No. 15/482,435, dated Jul. 27, 2017, Tennincan et al., "Portable Medical Device Protectors", 8 pages.

Brazilian Office Action dated Aug. 7, 2019 for Brazilian Patent Application No. BR1120120046950, a counterpart of U.S. Pat. No. 8,778,387, 4 pages.

Japanese Office Action dated Oct. 1, 2019 for Japanese Patent Application No. 2014-555816, a counterpart foreign application of U.S. Pat. No. 9,039,967, 4 pages.

\* cited by examiner

ADHESIVE PATCH WITH ANTIMICROBIAL COMPOSITION

CROSS REFERENCE TO RELATED APPLICATION

This claims priority to U.S. Provisional Patent Application No. 61/595,635 filed on Feb. 6, 2012 entitled "Antiseptic Applicators and Protective Devices," which is hereby incorporated by reference in its entirety.

BACKGROUND

Healthcare acquired infection (HAI) has been recognized as a significant cause of preventable mortality and morbidity. In the United States, HAI annually costs nearly 99,000 lives and billions of dollars in additional treatment and hospitalization. Klevens, et al., *Estimating Health Care-Associated Infection and Deaths in U.S. Hospitals*, 2002, Public Health Reports, Vol. 122, p. 160, 2007. Contamination of intravascular catheters, surgical sites and invasive procedure sites, frequently leads to device removal and replacement, prolonged parenteral antimicrobial therapy, and extended hospitalizations and rehabilitation.

The spread of multi-antimicrobial resistant organisms frequently are spread by healthcare providers' hands or medical equipment, from one colonized or infected patient to other susceptible patients. Surgical site infections may result from inadequate antiseptic preparations of the skin. Widespread use of chlorhexidine gluconate (CHG) for routine washing and wiping of pre-operative sites, has led to the increased incidence of resistant *Staphyloccus aureus*, both to methicillin (MRSA) and CHG, in some hospital environments.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items or features.

DETAILED DESCRIPTION

Overview

This disclosure describes medical applicators and patches designed to reduce and/or prevent infections. In one embodiment, the disclosure describes example patches comprising an impermeable backing having an adhesive located around a perimeter of the backing. The adhesive configured to allow the backing to removably attach to a surface (e.g., human skin or animal tissue). The impermeable backing further coupled to a permeable layer located interior to the adhesive and saturated with an antimicrobial agent.

The detailed discussion below begins with a section entitled "Example Antimicrobial Composition", which describes in detail an example antimicrobial composition that may be included in the adhesive patches described herein. Next, the disclosure describes "Example Adhesive Patch". Next, an "Example Process" for operating an example adhesive patch is described. Finally, the disclosure concludes with a brief "Conclusion."

This overview, including section titles, is provided to introduce a selection of concepts in a simplified form that are further described below. The overview is provided for the reader's convenience and is not intended to limit the scope of the claims, nor the proceeding sections.

Example Antimicrobial Composition

In one example implementation, antimicrobial compositions that may be used in connection with the approaches described herein may include those described in, for example, International Patent Application No. PCT/US2011/022150, filed Jan. 21, 2011, to Tennican et al., and, U.S. Non-Provisional patent application Ser. No. 13/688,078, filed Nov. 28, 2012, to Tennican, which are incorporated herein by reference. For example, the antimicrobial compositions may include water ($H_2O$), a strong and non-toxic chelating agent such as ethylenediaminetetraacetic acid (EDTA)(e.g., disodium EDTA, calcium disodium EDTA, magnesium EDTA, potassium EDTA, gallium EDTA) or sodium citrate (or acids, salts, derivatives, or other forms of EDTA or sodium citrate), a short-chain monohydric alcohol (e.g., ethanol with a molecular formula of $C_2H_5OH$ and an empirical formula of $C_2H_6O$), and a strong, small molecule oxidizing agent such as hydrogen peroxide ($H_2O_2$). In one specific example, the compositions may consist essentially of water, EDTA, ethanol, and hydrogen peroxide. Additional ingredients can include thickeners, gellants, surfactants, foamers and/or foam stabilizers. However, in other examples, other antimicrobial compositions may be used in combination with the applicators and patches described in this disclosure.

The antimicrobial compositions may be in a liquid form or a gel form, and may be combined with one or more carriers or diluents, depending on the needs of a specific application. For example, if the antimicrobial composition is used as a cleaning agent the antimicrobial composition may be in a liquid form. In that case, the concentration of the various constituents may depend on, for example, a desired level of sanitation and/or disinfection, whether the composition is being applied directly to living tissue or to a medical device, and/or to avoid irritation of tissue to which the composition will be applied directly or indirectly (e.g., via a medical device to which the composition is or was applied).

In addition to providing disinfection at the time of the application, the antimicrobial compositions may also provide a lasting barrier against contamination. For example, even after volatile constituents of the composition (e.g., water, alcohol, hydrogen peroxide, etc.) have evaporated, the chelating agent may remain on the treated surfaces (e.g., multiple use vial or port cleaning/protecting device, stethoscope, fingers, surrounding tissue, etc.) as a barrier that will provide antibacterial, antifungal or sporicidal (e.g., preventing germination of the spores), anti-parasitic, spermicidal or spermiostatic (e.g., decrease the motility of spermatozoon) and antiviral qualities. By robbing the environment of components (e.g., iron, magnesium, and manganese) that are needed for the bacteria (e.g., methicillin-resistant *Staphylococcus aureus* (MRSA), *Pseudomonas aeruginosa* and other resistant bacteria), spores, parasites, fungus and viruses to reproduce, the chelating agent provides a lasting defense to contamination even after other constituents of the antimicrobial composition have evaporated. Furthermore, the hydrogen peroxide in the antimicrobial compositions may induce a charge on a surface of materials (e.g., silicone materials) to which the antimicrobial compositions are applied, which make the materials more resistant to bacteria or other microorganisms.

The antimicrobial composition described above may also provide a visual indication of contamination when applied to a surface or material, such indication may allow users to identify and clean surfaces to prevent infection.

The term "about" or "approximate" as used in context of describing the example antimicrobial composition is to be construed to include a reasonable margin of error that would be acceptable and/or known in the art.

Example Adhesive Patch

Various adhesive patches are describes herein. Example adhesive patches are described generally with reference to FIGS. 1A, 1B, and 2.

Figure 1A:
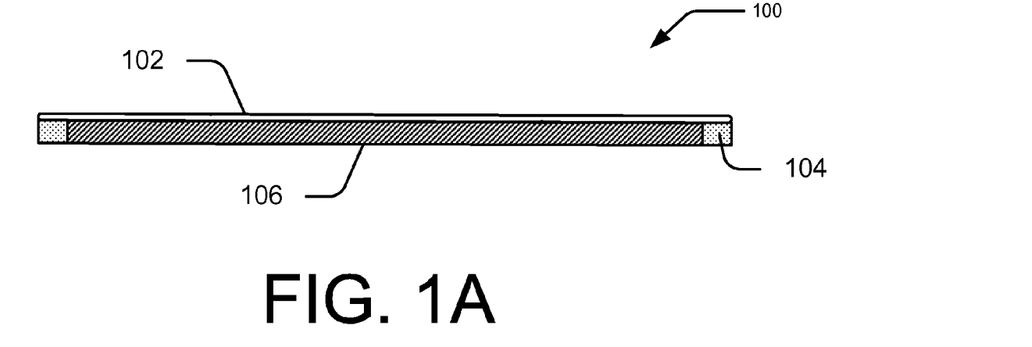
FIG. 1A illustrates a cross-sectional view of an example adhesive patch.

FIG. 1A illustrates a cross-section view of an embodiment of an example adhesive patch that may be used to prepare and/or protect a site or surface. In this embodiment, an adhesive patch 100 may be applied to an area of skin prior to the beginning of a medical procedure, thus creating, and/or maintaining an uncontaminated skin zone while simultaneously allowing surgical entry and visibility. In some embodiments, the example adhesive patch 100 comprises an impermeable backing layer 102 having an adhesive material 104 located around the perimeter of the backing. The impermeable backing may further be coupled to a permeable layer 106 which may contain an antimicrobial agent. The permeable layer 106 may be located interior from the adhesive material on the impermeable backing.

In some embodiments, the impermeable backing 102 and permeable layer 106 of the example adhesive patch 100 may be composed of a sterile, translucent/semi-transparent, radiolucent, hypoallergenic, waterproof, and/or elastic material. For example material of the impermeable backing 102 of patch 102 may include, but not limited to, polyethylene, aluminum oxide, silicone oxide coated polymeric films, polypropylene, polysilicone, polytetrafluoroethylene, polyvinyl chloride, mylar, urethane polymer, acrylate polymer, or mixtures thereof. Where example materials for the permeable layer 106 include, but are not limited to, starch polymer, cellulosic gel, polyethylene foam, polyurethane foam, silicone open cell foam, or mixtures thereof. A level of transparency may allow a user to monitor a site while the patch is in place and also may allow a medical procedure (e.g., a radiological exam, an arthroscopic procedure, or the like) to proceed while the patch remains in place over the site. In some embodiments, elasticity may allow the patch to conform to various contours of the application surface (e.g., a human knee, arm, chest, or the like).

Figure 1B:
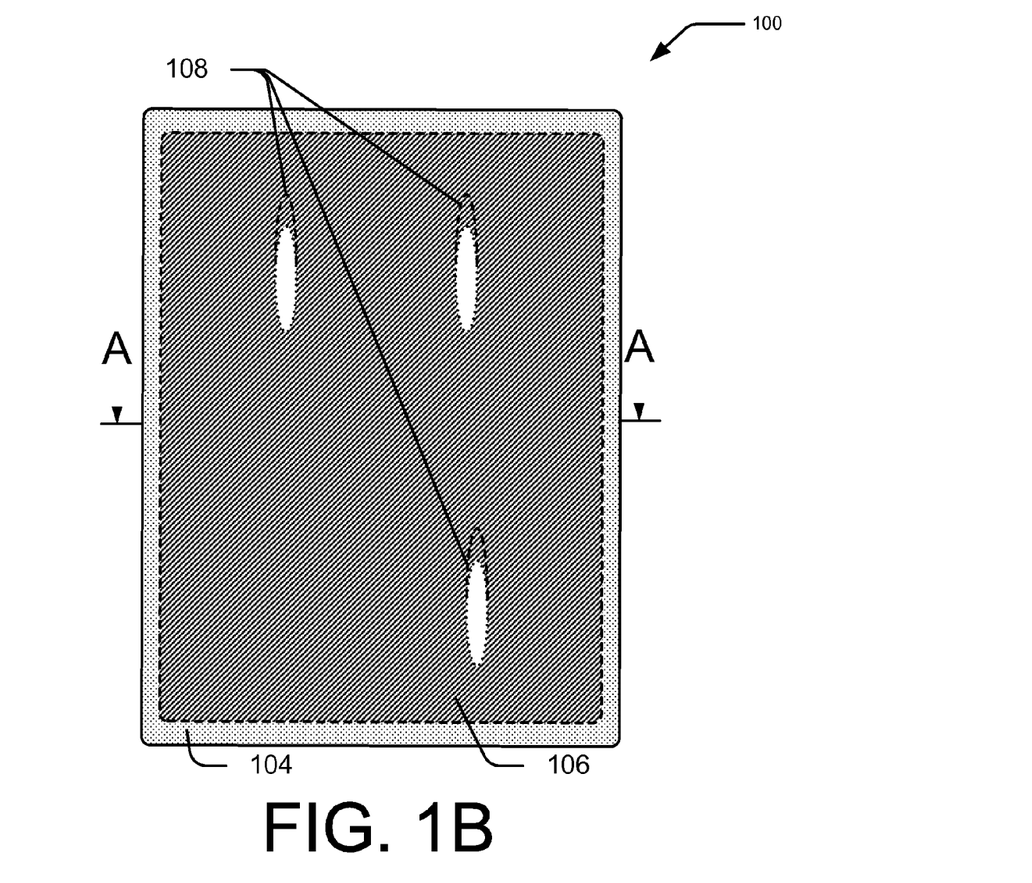
FIG. 1B illustrates an adhesive side view of an example adhesive patch.

FIG. 1B illustrates an adhesive side view of an example adhesive patch 100. The example adhesive patch 100 is shown as having a rectangle shape, although alternative shapes are contemplated such as, for example, a round shape, a rectangular shape, an oval shape, a polygon shape, or any other shape to accommodate the contours of human or animal skin.

In some embodiments, example adhesive patch 100 may have an adhesive material positioned around the exterior perimeter of the patch 100 and a permeable layer 106 positioned interior to the adhesive material 104. The adhesive material 104 may comprise any one or more of hypoallergenic, medical grade adhesives. Additionally, adhesive material 104 may be positioned on the perimeter of the impermeable backing layer in any width suitable to secure the patch to a surface. For example, a greater amount of adhesive material may be necessary to affix a larger patch or to affix a patch to a surface prone to movement (e.g., a knee, elbow, shoulder, or the like).

In some embodiments, the permeable layer may contain or be at least partially coated with the antimicrobial composition described in the preceding section. In some embodiments, the antimicrobial composition may be formulated as a liquid or a gel in any number of concentrations. In some embodiments, where the antimicrobial composition is a gel, the adhesive patch 100 may be constructed without the permeable layer 106, In other embodiments, the antimicrobial composition may be combined with the adhesive material. In yet other embodiments, the adhesive material 104 may cover the entire underside shown in FIG. 1B. In this embodiment, the patch 100 may be constructed with or without the permeable layer 106.

The adhesive patch 100 may establish the uncontaminated zone by antimicrobial action when the patch is placed on a desired surface. In some embodiments, the adhesive patch could be applied at a sufficient time before the medical procedure to allow the antimicrobial action to work more thoroughly. The adhesive patch may additionally or alternatively be placed on the skin to maintain the uncontaminated zone after the skin is otherwise prepared for the medical procedure. In some embodiments, placing the adhesive patch over a desired incision site and allowing the patch to remain on the site for an extended period of time may permit the antimicrobial composition to penetrate skin and tissue layers more so than would be possible by using a simple topical application of a very strong antimicrobial before starting the incision.

As illustrated in FIG. 1B, the adhesive patch 100 may comprise one or more removable windows 108 at positions corresponding to incision and/or penetration sites. The adhesive patch 100 may be placed/aligned over a desired site so that the one or more removable windows 108 correspond with one or more incision and/or penetration sites. At the time of incision and/or penetration, a user may peel or otherwise remove the one or more windows to expose the site. For example, as illustrated in FIG. 1B, a user may peel away the three removable windows 108 which may correspond to the three incision or penetration sites for a common arthroscopic knee surgery.

Figure 2:
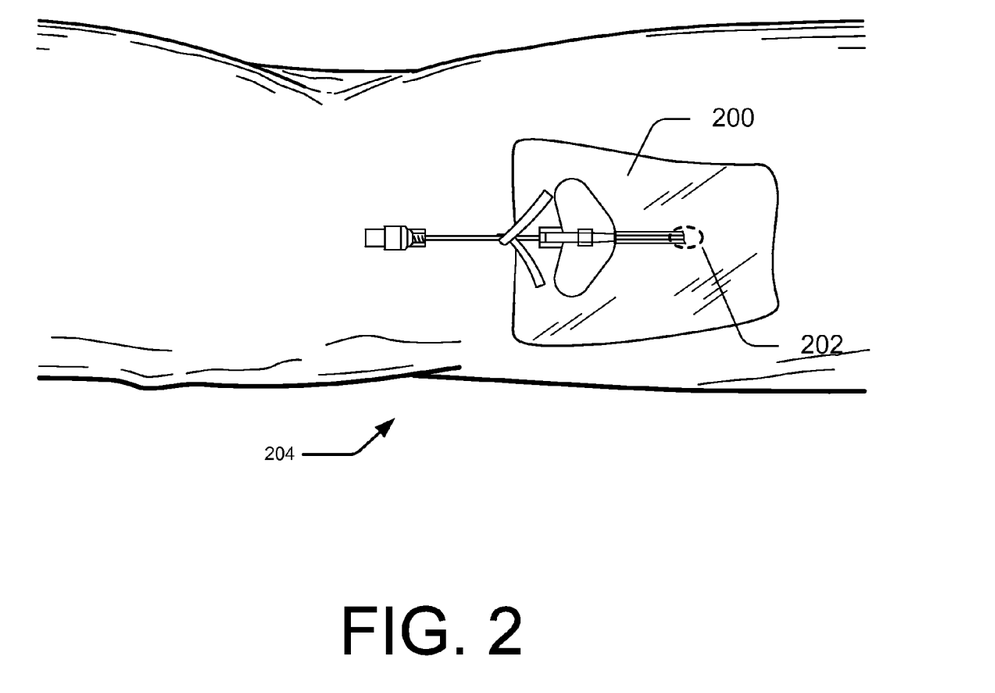
FIG. 2 illustrates an example adhesive patch as used on the arm of a human.

FIG. 2 illustrates an example adhesive patch 200 that may be manufactured to comprise one or more pattern markings 202 on the adhesive patch to act as a template for the incision and/or penetration sites for a particular medical procedure. For example, the adhesive patch may be manufactured with a marking to designate the needle puncture site for the placement of a central venous catheter, or other IV components. In this embodiment, a user or health practitioner may place the adhesive patch over a human arm 204 so the marking on the patch aligns with the needle puncture site. In other embodiments, the adhesive patch 200 (or any other patch described herein) may allow a user to make any marking to designate one or more personalize or specific penetration site(s).

Details of the medical device described with respect to FIGS. 1A, 1B, and 2 may additionally or alternatively be applied to the example protective devices described in U.S. patent application Ser. No. 12/874,188, filed Sep. 1, 2010 to Tennican et al., which is incorporated herein by reference.

Example Process

Figure 3:
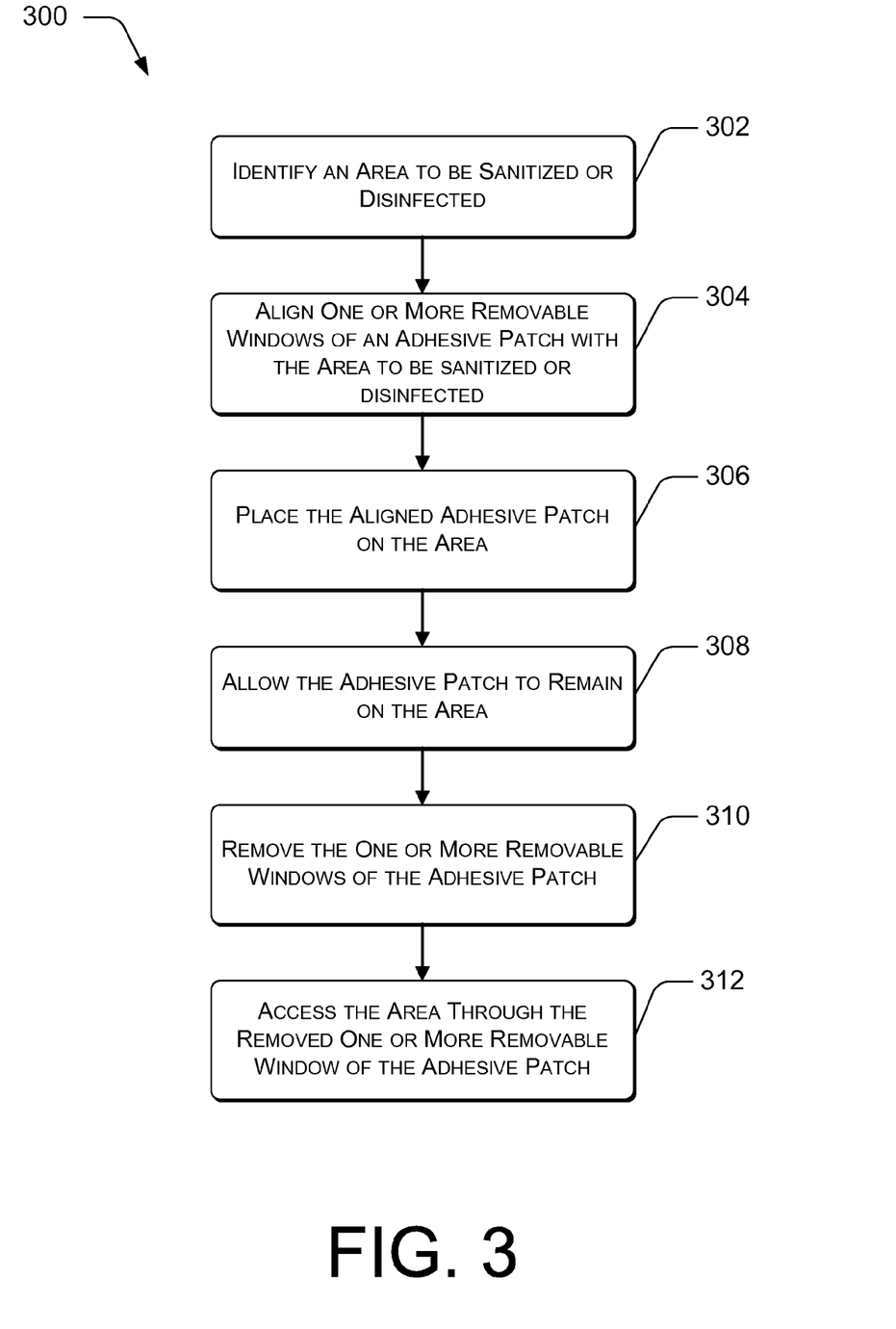
FIG. 3 is a flow diagram showing an example process for operating an example adhesive patch.

FIG. 3 illustrates an example process 300 for execution of the techniques described above of operating an example adhesive patch. The process 300 is illustrated as a logical flow graph. The order in which the operations are described is not intended to be construed as a limitation, and any number of the described operations can be combined in any order and/or in parallel to implement the process.

At operation 302, an area to be sanitized or disinfected may be identified. For example, a user may identify an area of such as human skin that needs to be sanitized prior to beginning a medical procedure.

At operation 304, an adhesive patch having an antimicrobial composition may be applied to the area by aligning one or more removable windows of the adhesive patch with one or more access sites on the area to be sanitized or disinfect. In the context of FIG. 1B, a user may align the removable windows 108 of adhesive patch 100 with one or more incision sites corresponding to the incision sites for a particular medical procedure.

At operation 306, the aligned adhesive patch may be placed on the area to be sanitized or disinfected. As described in the context of adhesive patch 100, placing the adhesive patch over the area may allow the antimicrobial composition to come into contact with the area and one or more contaminants.

At operation 308, the adhesive patch may be allowed to remain on the area to be sanitized or disinfected. As described in the context of adhesive patch 100, allowing the adhesive patch to remain over the area may, for example, allow the antimicrobial composition to penetrate deeper into the skin and tissue layers and/or allow the antimicrobial composition to continue disinfecting or sanitizing.

At operation 310, the one or more removable windows aligned with the one or more access sites on the area may be removed. In the context of FIG. 1B, a user may peel away the three removable windows 108 to expose the one or more access sites on the area.

Finally at operation 312, the one or more access sites on the area may be accessed through the removed one or more windows of the adhesive patch.

CONCLUSION

Although the disclosure describes embodiments having specific structural features and/or methodological acts, it is to be understood that the claims are not necessarily limited to the specific features or acts described. Rather, the specific features and acts are merely illustrative some embodiments that fall within the scope of the claims of the disclosure.

What is claimed is:

1. A method for creating an area free of one or more contaminants comprising:
   identifying the area to be sanitized or disinfected;
   applying an adhesive patch to the area, the adhesive patch comprising:
   an impermeable backing layer, the impermeable backing including one or more removable windows, wherein each of the one or more removable windows are removable to expose one or more access sites on the area;
   an adhesive boundary fixed around an exterior edge of the impermeable backing layer;
   a permeable layer coupled to the impermeable backing layer and interior to the adhesive boundary; and
   an antimicrobial composition retained by the permeable layer.

2. The method as recited in claim 1, wherein the impermeable backing layer further comprises one or more markings, wherein each of the one or more marking represent the one or more access sites on the area.

3. The method as recited in claim 2, wherein applying the adhesive patch to the area further comprises:
   aligning the one or more markings with the one or more access sites on the area to be sanitized or disinfected;
   placing the aligned adhesive patch on the area to be sanitized or disinfected allowing the antimicrobial composition to come in contact with the one or more contaminants;
   allowing the adhesive patch to remain on the area;
   accessing the one or more access sites through the one or more markings.

4. The method as recited in claim 1, wherein the antimicrobial composition is effective to sanitize or disinfect the area of the one or more contaminants, the one or more contaminants including at least one of methicillin-resistant *Staphylococcus aureus* (MRSA), *Pseudomonas aeruginosa* or other bacteria.

5. The method as recited in claim 1, wherein the area to be sanitized or disinfected comprises a portion of human skin.

6. The method as recited in claim 1, wherein applying the adhesive patch to the area further comprises:
   aligning the one or more removable windows of the adhesive patch with the one or more access sites on the area to be sanitized or disinfected;
   placing the aligned adhesive patch on the area to be sanitized or disinfected allowing the antimicrobial composition to come in contact with the one or more contaminants;
   allowing the adhesive patch to remain on the area:
   removing the one or more removable windows aligned with the one or more access sites; and
   accessing the one or more access sites.

7. The method as recited in claim 1, wherein the antimicrobial composition comprises:
   5 to 50 mg/ml of ethylenediaminetetraacetic acid (EDTA);
   at most 70% ethanol, by volume;
   at most 7.5% hydrogen peroxide, by volume; and
   water.

8. A medical patch for creating or maintaining an area of human issue free of one or more contaminants comprising:
   an adhesive fixed to a perimeter of an impermeable backing, the impermeable backing including one or more removable windows, wherein each of the one or more removable windows are removable to expose one or more access sites on the area;
   a permeable layer coupled to the impermeable backing interior to the adhesive; and
   an antimicrobial agent located within the permeable layer, the antimicrobial agent comprising at least one or more of water, hydrogen peroxide, a chelator, or an alcohol.

9. The patch as recited in claim 8, wherein the antimicrobial agent is effective to disinfect an area of human skin of the one or more contaminants, the one or more contaminants comprising at least one of a bacterium, a spore, a parasite, a fungus, a virus, a bodily fluid or a combination thereof.

10. The patch as recited in claim 9, wherein the bacterium includes at least one of methicillin-resistant *Staphylococcus aureus* (MRSA), *Pseudomonas aeruginosa* or other bacteria.

11. The patch as recited in claim 8, wherein the each of the one or more access site correspond to one or more locations on the human tissue where penetration is desired for a medical procedure.

12. The patch as recited in claim 8, wherein the chelator comprises one of ethylenediaminetetraacetic acid (EDTA), salts of EDTA, sodium citrate, or another biocompatible chelator.

13. The patch as recited in claim 8, wherein the antimicrobial agent comprises:
   5 to 50 mg/ml of ethylenediaminetetraacetic acid (EDTA);
   at most 70% ethanol, by volume;
   at most 7.5% hydrogen peroxide, by volume; and
   water.

14. A medical patch comprising:
   a transparent impermeable backing layer, wherein the transparent impermeable backing layer includes
      one or more removable windows, wherein each of the one or more removable windows are removable to expose one or more access sites;
   an adhesive attached to a perimeter of the impermeable backing layer; and
   an antimicrobial gel located interior to the adhesive perimeter on the impermeable backing layer, the antimicrobial gel comprising at least one or more of water, hydrogen peroxide, a chelator, or an alcohol.

15. The medical patch as recited in claim 14, wherein the antimicrobial gel is effective to disinfect or sanitize an area of human skin of one or more of a bacterium, a spore, a parasite, a fungus, a virus, a bodily fluid or a combination thereof.

16. The medical patch as recited in claim 15, wherein the bacterium include at least one of methicillin-resistant *Staphylococcus aureus* (MRSA), *Pseudomonas aeruginosa* or other bacteria.

17. The medical patch as recited in claim 14, wherein the one or more access sites correspond to an incision site or a penetration site for a predetermined medical procedure.

18. The medical patch as recited in claim 14, wherein the antimicrobial gel comprises:
   5 to 50 mg/ml of ethylenediaminetetraacetic acid (EDTA);
   at most 70% ethanol, by volume;
   at most 7.5% hydrogen peroxide, by volume; and
   water.

19. The medical patch as recited in claim 14, wherein the transparent impermeable backing layer comprises polyethylene, silicone oxide coated polymeric films, polypropylene, polysilicone, polytetrafluoroethylene, polyvinyl chloride, mylar, urethane polymer, acrylate polymer, or mixtures thereof.

* * * * *